United States Patent [19]
Wheeler et al.

[11] Patent Number: 5,925,790
[45] Date of Patent: Jul. 20, 1999

[54] PREPARATION OF SUBSTITUTED AROMATIC AMINES

[75] Inventors: Edward L. Wheeler, Watertown; Russell E. Malz, Jr., Naugatuck; Mark W. Simon, Waterbury, all of Conn.

[73] Assignee: Uniroyal Chemical Company, Inc., Middlebury, Conn.

[21] Appl. No.: 08/816,612

[22] Filed: Mar. 13, 1997

[51] Int. Cl.[6] .................................................. C07C 209/02
[52] U.S. Cl. ......................... 564/408; 556/138; 564/415; 564/434
[58] Field of Search .................................... 564/408, 415, 564/434

[56] References Cited

U.S. PATENT DOCUMENTS

| | | | |
|---|---|---|---|
| 3,336,386 | 8/1967 | Dovell et al. | 260/576 |
| 5,117,063 | 5/1992 | Stern et al. | 564/398 |
| 5,728,882 | 3/1998 | Wheeler et al. | 564/408 |

FOREIGN PATENT DOCUMENTS

| | | |
|---|---|---|
| 0138524 | 4/1970 | Czech Rep. . |
| 0261096 | 3/1988 | European Pat. Off. . |
| 0272238 | 6/1988 | European Pat. Off. . |
| 1440767 | 6/1976 | United Kingdom . |

OTHER PUBLICATIONS

Reactions of Disodium Pentacyanoamminoferrate With Aromatic Amines. Part II.The Preparation and *Journal of The Chemical Society,* E.F.G. Herington, 1958, Letchworth G.B., pp. 4683–4688.

Determination of Hexacyanoferrate Based On Its Catalytic Influence on The Oxidation of P–phenylene, *Chemical Abstracts,* Nickel Ulrich, et al, vol. 112, No. 22, May 28, 1990, abstract No. 210156n, Fresenius. J. Anal. Chem., vol. 336, No., 4,1990, pp. 316–319.

"Anodic Oxidations of Aromatic Amines, III, Substituted Anilines in Aqueous Media", Jeff Bacon and R. N. Adams, *Journal of the American Chemical Society,* pp. 6596–6599, 1968.

Reactions of Disodium Pentacyanoammoniferrate With Aromatic Amines, E. F. G. Herington, in *Journal Chem. Soc.,* p. 2747, 1956.

"Sodium Pentacyanoamminoferrate (III)", G. Brauer, *Handbook of Preparative Inorganic Chemistry,* 2nd ed. vol. II, Academic Press, New York, N.Y. 1965, pp. 1511–1512.

"Reactions of Disodium Pentacyanoamminoferrate With Aromatic Amines", E. F. G. Herington, in *Journal Chem. Soc* p. 4683–88, 1958.

*Primary Examiner*—Richard L. Raymond
*Attorney, Agent, or Firm*—Raymond D. Thompson

[57] ABSTRACT

A method for producing aromatic amines such as N-phenyl-p-phenylenediamine is disclosed wherein an amine substituted aromatic such as aniline is oxidized with oxygen or hydrogen peroxide in the presence of a preferred trisodium pentacyano ferrate(II) complex containing various water soluble ligands, such as ammonia, mono alkyl amine, dialkyl amines, and trialkyl amines. The complex is subsequently catalytically reduced by hydrogenation using certain heterogeneous metal catalysts to yield the desired aromatic amine.

17 Claims, No Drawings

PREPARATION OF SUBSTITUTED AROMATIC AMINES

BACKGROUND OF THE INVENTION

1. Field of the Invention

The present invention relates to methods for the production phenyl-p-phenylenediamine (PPDA) and higher amines of structural formula (I) below from the starting material of structural formula(II) below. More particularly it relates to a method for preparing PPDA wherein aniline is oxidized in the presence of trisodium pentacyano ferrate(II)complexes containing various water soluble ligands, such as ammonia, mono alkyl amine, dialkyl amines, and trialkyl amines, and utilizing oxygen or hydrogen peroxide as the oxidizing agents. The complex is then reduced by hydrogenation using suitable heterogeneous metal catalysts.

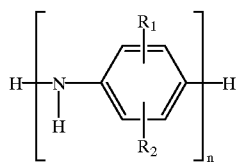

(I)

wherein n equals 2 to 5, and $R_1$ and $R_2$ are as set forth below

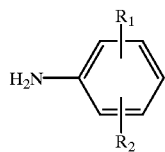

(II)

$R_1$ and $R_2$ may be the same or different, must be ortho or meta to the amino group, and may be hydrogen, $C_1$–$C_4$ alkyl, $C_1$–$C_4$ alkoxy, halogen, cyano, carboxylate salts and amides of carboxylic acids or mixtures thereof.

The invention relates to the production of PPDA with the ability to recycle the transition-metal complex, high selectivity and yield. The conversion of aniline to N-phenyl-p-phenylenediamine is in the range of 40–85%. The yield of PPDA ranges from 91 to 97%. The method of this invention is also cost effective and produces no environmentally undesirable byproducts.

2. Background of the Related Art

The production of p-phenylenediamine and its derivatives is widespread and its uses are widely known. In U.S. Pat. No. 5,117,063, Stern et al., disclose various methods of preparing N-phenyl-p-phenylenediamine wherein aniline and nitrobenzene are reacted under specific conditions.

In other publications, the oxidative dimerization of aniline to produce N-phenyl-p-phenylenediamine is disclosed. British patent No. 1,400,767 and European patent 0-261096 utilize an alkali metal ferricyanide whereas European patent 0-272-238 utilizes a hypohalite oxidizing agent. None of these processes are very selective, nor do they give good conversions.

J. Bacon and R. N. Adams in J. Am. Chem. Soc.,90 p 6596 (1968) report the anodic oxidation of aniline to N-phenyl-p-quinonediimine but no conversions or yields are given. E. Herrington, in J.Chem.Soc. p4683 (1958) reports the oxidative dimerization of aniline with disodium pentacyanoamminoferrate (III) to form a complex containing N-phenyl-p-phenylenediamine which is then reduced chemically with reducing agents such as hydrazine hydrate, sodium dithionate, sodium hydrogen sulfite and hydrogen sulfide. The use of the trisodium pentacyanoamminoferrate (II) complex and catalytic reduction with hydrogen of this invention distinguish over this publication and the differences result in a significantly improved process. The stoichiometry of the instant invention is much improved over Herrington since higher ratios of aniline to complex can be used in the process disclosed herein.

It is therefore an object of this invention to provide a method for the production of N-phenyl-p-phenylenediamine and related compounds. It is a further object of this invention to disclose a method for the production of such compounds via an aqueous process that allows the easy removal of unreacted aniline and subsequent separation of the reconstituted starting complex from the desired end product [formula (I)] after reduction giving a process which is commercially viable, involving both low cost and recyclability.

It is still a further object of this invention to provide a process that favors the p-phenylenediamine product, with both high yield and good selectivity. It is yet a further object of this invention to furnish a process with produces less waste and effluent streams. A still further objective is the production of phenylenediamine derivatives which may be used industrially as antidegradants made from the high purity products of the process of this invention.

SUMMARY OF THE INVENTION

The present invention is directed to an improved method for preparation of substituted aromatic amines of formula (I) comprising the steps of: a) oxidizing an aromatic amine of formula (II) in the presence of a metal pentacyano ferrate (II) complex to form an arylenediaminopentacyanoferrate complex, said metal being selected from the group consisting of potassium and sodium; and b) catalytically reducing said arylenediamino-pentacyanoferrate complex with hydrogen using a heterogeneous metal catalyst, producing the corresponding substituted aromatic amine of formula (I).

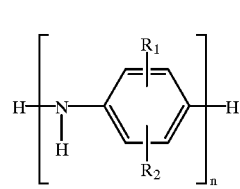

(I)

wherein n equals 2 to 5, and $R_1$ and $R_2$ are as set forth below

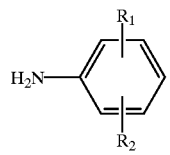

(II)

$R_1$ and $R_2$ may be the same or different, must be ortho or meta to the amino group, and may be hydrogen, $C_1$–$C_4$ alkyl, $C_1$–$C_4$ alkoxy, halogen, cyano, carboxylate salts and amides of carboxylic acids or mixtures thereof.

The most preferred embodiment is directed to a process which oxidizes aniline in the presence of trisodium pentacyano ferrate (II) complexes containing various water soluble ligands, such as ammonia, mono alkyl amine, dialkyl amines, trialkyl amines and the like. Oxidizing agents may be oxygen or hydrogen peroxide. The N-phenyl-p-phenylenediamino pentacyano ferrate complex is then reduced with hydrogen using a heterogeneous metal catalyst, which may be supported or not supported. Suitable supports could include those known to the art such as, for example, carbon or alumina. The mixture of aniline and N-phenyl-p-phenylenediamine is then extracted with a suitable solvent after filtration of the heterogenous catalyst. Preferred solvents are environmentally friendly, water-immiscible, and easily recyclable. The aqueous layer containing the pentacyano ferrate (II) complex is then recycled.

DETAILED DESCRIPTION OF THE INVENTION

A preferred method of the present invention for producing N-phenyl-p-phenylenediamine (PPDA) involves the steps of a) the oxidation of aniline in the presence of trisodium pentacyano ferrate (II) complexes with the optional use of a heterogeneous metal catalyst; followed by b) reduction of the N-phenyl-p-phenylenediamino-pentacyano ferrate complex with hydrogen using a heterogeneous metal catalyst.

In most cases, both steps (a) and (b) will use the same heterogeneous catalyst. In the first step, any suitable oxidant including either oxygen or hydrogen peroxide may be used as the oxidizing agent. Oxygen is the preferred oxidizing agent. Still more preferred is the use of oxygen under pressure and at elevated temperatures which will increase the rate of oxidation and facilitate the completion of step a.

The metal pentacyano ferrate (II) complexes useful in this invention must be of a water soluble type having water soluble ligands as a part of the complex. Preferred metals are the alkali metals such as sodium or potassium. The most preferred, trisodium pentacyano ferrate (II) complex containing various water soluble ligands, is illustrative of the class of complexes useful. These ligands may be ammonia, monoalkyl amines, dialkyl amines, or trialkyl amines. A preferred structure for this preferred complex is $Na_3[Fe(CN)_5NH_3 \cdot xH_2O]$, or its dimer.

In the second step of the preferred reaction, the N-phenyl-p-phenylenediamino-pentacyano ferrate complex is reduced with hydrogen using a heterogeneous metal catalyst. This catalyst is selected from the heterogeneous metals of Group VIII such as palladium, platinum, ruthenium, rhodium, or nickel. The catalyst may or may not be supported. If supported, the supports may be carbon, alumina, and the like, many of which are known to those familiar with the art.

The mixture of aniline and PPDA that is the product of the reaction is extracted with a suitable solvent. Then the heterogeneous catalyst is filtered off. Suitable solvents include those that are water-immiscible and easily recyclable. The aqueous layer containing the pentacyano ferrate (II) complex is then recycled.

The compounds of this invention can be synthesized advantageously by the following general method. The preferred method for the preparation of PPDA is contained in the examples that follow.

The first step of a preferred process of this invention involves dissolving sodium pentacyanoammino ferrate (II) in water. The synthesis of sodium pentacyanoammino ferrate (II) is known. It was prepared according to the method of G. Brauer "Handbook of Preparative Inorganic Chemistry", 2nd ed. Vol II, academic Press, New York, N.Y. 1965 p 1511.

Novel method for preparation of Trisodium pentacyano ammino ferrate (II)

An alternate method for preparation of trisodium pentacyano ammino ferrate(II) is the concurrent addition of aqueous solution of ferrous chloride tetrahydrate, stabilized with hypophosphorous acid, and sodium cyanide in the ratio of 1 to 5 equivalents to an aqueous solution of ammonium hydroxide. The aqueous solution of ammonium hydroxide may contain anywhere from one equivalent based on the ferrous chloride to a large excess. The preferred range is two to ten equivalents and the most preferred is three to six equivalents of ammonium hydroxide.

The concurrent additions are done over one to three hours and the solution is then filtered if necessary to remove small amounts of iron hydroxides and the complex is precipitated by adding isopropanol or any convenient water soluble organic solvent. The complex may be dried or redissolved in water without drying and used directly. The excess ammonia and isopropanol are recovered.

For the addition of aniline, a water miscible organic solvent may be added to help solubilize the aniline. In the instant invention, this reaction may be run without organic solvent. Examples of such solvents are ethylene glycol, propylene glycol, diethylene glycol, and triethylene glycol. Two equivalents of aniline are added and the mixture is then oxidized. Oxygen or hydrogen peroxide are two possible oxidizing agents that can be used. A heterogeneous metal catalyst may be added prior to the oxidation.

In the second step of the process of this invention, the oxidized complex containing the N-phenyl-p-phenylenediamino ligand is subjected to hydrogenation in the presence of a heterogeneous metal catalyst. This may be carried out without added solvent, or in the presence of a suitable water immiscible solvent. Possible solvents in this category include butyl acetate, hexanol, 2-ethyl-1-butanol, hexyl acetate, ethyl butyl acetate, amyl acetate, methyl isobutyl ketone or aniline and the like. After hydrogenation, the heterogeneous catalyst is removed by filtration and the organic layer separated. The solvent, aniline, and N-phenyl-p-phenylenediamine are recovered by distillation. The sodium pentacyanoammino ferrate(II) is then recycled.

The reaction is best carried out at a pH equivalent to the pH of the solution containing the dissolved complex in water. The pH is adjusted, when necessary, after each recycle of the complex by adding ammonia to the solution in order to maintain a pH equivalent to the initial pH of the solution at the start of the process. This adjustment of pH is achieved by the addition of an appropriate base, for example, ammonium hydroxide or ammonia, the ligand used in the complex. A more preferred range of pH is from 10 to 12. A pH equivalent to the pH of the dissolved complex, which is dependant on concentration of the solution is preferred.

Oxygen and hydrogen pressures may be in the range of from about 1 atmosphere to 100 atmospheres. A preferred range of these pressures would be from about 2 to about 75 atmospheres. A preferred range of these pressures would be from about 50 to about 75 atmospheres, or about $5.0 \times 10^6$ to about $7.5 \times 10^6$ $Nm^{-2}$. Similar pressures are used for the reduction reaction with hydrogen.

Temperatures may range up to the point where the complex looses stability which currently is believed to be from about 5° C. to about 65° C. in a closed system. Although the reaction can be carried out at lower temperatures, the rate of reaction of the oxidation step is significatnly lower. The preferred operation temperature for the oxidation reaction is between 30° C. and 55° C., and most preferred range is between 45° C. and 55° C. The temperature used will require a balance of factors to maximize the reaction rate and yeild of the process. Higher temperatures than specified here will slowly degrade the complex. Low temperatures reduce the solubility of the complex and decrease the rate of reaction. The reducing step with hydrogen is conducted at a reaction temperature range from about 5° C. to about 60° C.

A number of ligands can be used instead of ammonia in the sodium pentacyano ferrate (II) complex. Ligands may be mono alkyl amines such as methyl, ethyl, propyl, or butyl amines, dialkyl amines such as dimethyl or diethyl amine and trialkyl amines such as trimethyl amine or triethyl amine. Other amines that can be used are N,N-dimethylaminoethanol, N,N,N',N'-tetramethylethylenediamine, and substituted or unsubstituted pyridine. A variety of other ligands can be used, limited only by their solubility, and their ability to be displaced by aniline and by their stability.

In this invention, sodium pentacyano ferrates (II) containing ligands other than ammonia were prepared by substitution of the ammonia complex with an excess of the appropriate ligand.

Among the heterogeneous metal catalysts that may be used are palladium-on-carbon, platinum on-carbon, ruthenium-on-carbon, rhodium-on-carbon, and Raney nickel. Supports other than carbon, such as alumina, Kieselguhr, silica, and the like can be used as well. Preferred among the catalysts that may be used are the noble metals. Still more preferred are supported noble metal catalysts. An even more preferred catalyst is platinum or palladium supported on carbon.

The recyclability of the pentacyanoammino ferrate complex is demonstrated in various examples of this invention. The recycling procedure may be carried out at temperatures ranging from 25° C. to 60° C., and most preferably between 45° C. and 55° C. The recyclability is useful with ligands other than ammonia in the pentacyano ferrate (II) complex, such as pentacyanotrimethylamino ferrate (II) or pentacyanoisopropylamino ferrate (II) complexes. Experimental details of the recyclability, including conversion and yield data, are presented in the examples.

Reductive alkylation of PPDA to produce antidegradants can be conducted by any one of various known methods known to those skilled in the art. See, for example, U.S. Pat. No. 3,336,386, which is herein incorporated by reference. Preferably, PPDA and a suitable ketone or aldehyde are reacted in the presence of hydrogen and a catalyst such as platinum sulfide with or without a support. Suitable ketones include methylisobutyl ketone, acetone, methylisoamyl ketone, and 2-octanone.

The following examples are intended to further illustrate the invention and are not intended to limit the scope of the invention in any manner whatsoever.

EXAMPLES

Example 1

The Oxidation of Aniline using Hydrogen Peroxide as the Oxidizing Agent(step a); and Hydrogen (with 5% Palladium/Carbon) as the Reducing Agent (step b) in the Preparation of PPDA The reaction of step a was run using 3.0 g of aniline, 6.0 g sodium pentacyanoammino ferrate (II), 300 ml of distilled water and 1.0 g of 5% palladium on charcoal(Pd/C) (50% wet) in a three-neck flask equipped with mechanical stirrer and addition funnel. Eight ml of 30% hydrogen peroxide (oxidizing agent) was added in 0.5 hours.

The heterogeneous catalyst was removed by filtration and the reaction mixture was transferred to a 1-l Magne-drive autoclave. 1.0 g of fresh Pd/C catalyst (50% water) was then added. The vessel was sealed, purged first with nitrogen and then with hydrogen and pressurized with hydrogen to about 1000 psig [69 atm or $6.9 \times 10^6$ $Nm^{-2}$]. The vessel was agitated at room temperature for 2.0 hours. Isopropyl acetate was added to the reaction mixture after venting and purging with nitrogen. The catalyst was removed by filtration and the organic solution was analyzed by gas chromatography using a Varian 3400 instrument equipped with a DB-I capillary column. The product N-phenyl-p-phenylenediamine (PPDA) was found in 74.3% conversion, and aniline was measured at 18.4%. The yield based on conversion of aniline was 91%.

Examples 2–6

The Oxidation of Aniline using Oxygen as the Oxidizing Agent(step a); and Hydrogen with Several Metal Catalysts as the Reducing Agent (step b) in the Preparation of PPDA Using the basic procedure depicted in Example 1, several reactions were run in a 1-liter Magne-Drive autoclave using 38.0 g. sodium pentacyanoammino ferrate (II), 18.6 g aniline, 2.0 g. metal catalyst 50.0 g. ethylene glycol and 150 g distilled water. The metal catalysts used in Examples 2–6 are supported Pd, Ru, Pt, Rh and Ni, respectively. In Examples 2–5, the heterogeneous catalysts are present at 5% by weight on carbon and they are used at 4.0 g and 50% water. In Example 6, the nickel is used as 50% Ni/Kieselguhr 2.0 grams dry.

The vessel was sealed, purged first with oxygen and pressurized to 400 psig [28 atm or $2.8 \times 10^6$ $Nm^{-2}$]. The vessel was agitated at room temperature for 2.5 hrs. After this agitation, the vessel was purged with nitrogen and then 100 ml of butyl acetate was pumped into the autoclave. The vessel was purged with hydrogen and then pressurized with hydrogen to 400 psig [28 atm or $2.8 \times 10^6$ $Nm^{-2}$]. The vessel was then agitated at room temperature for 1.0 hr. The ester solution was isolated and analyzed by HPLC. The nickel catalyst on Kieselguhr (Example 6) was found to be inactive.

Results of these Examples are presented in Table 1.

TABLE 1

| EXAMPLE | CATALYST G | CONVERSION % (a) | YIELD % (b) |
|---|---|---|---|
| 2 | 5% Pd/C 4.0 g 50% $H_2O$ | 69 | 93 |
| 3 | 5% Ru/C 4.0 g 50% $H_2O$ | 30 | 87 |
| 4 | 5% Pt/C 4.0 g 50% $H_2O$ | 72 | 95 |
| 5 | 5% Rh/C 4.0 g 50% $H_2O$ | 51 | 96 |
| 6 | 50% Ni/Kieselguhr 2.0 g Dry | 3 | 88 |

Notes for Table 1:
(a) N-Phenyl-p-phenylenediamine analyses by reverse phase HPLC using water-acetonitrile gradient with a Perkin-Elmer series 410 LC pump, a LC 235 Diode Array detector using a 3.3 cu. pecosphere ™ 3C18 column.
(b) N-Phenyl-p-phenylenediamine yield based on converted aniline.

Example 7

Oxidation of Aniline using Oxygen and no Metal Catalyst (step a); and Reduction with Hydrazine (step b) in the preparation of PPDA.

In a manner similar to the previous examples, step (a) of the reaction was run in a 1-liter Magne-Drive autoclave using 24 g of sodium pentacyanoammino ferrate (II), 12.8 g of aniline, 100 ml of ethylene glycol and 300 ml of distilled water. The vessel was sealed, purged with nitrogen, then oxygen and pressurized with oxygen to 400 psig [28 atm or $2.8 \times 10^6$ Nm$^{-2}$]. The vessel was agitated at 15–20° C. with cooling to control the temperature for six hours.

Following oxidation, a one ml sample was removed from the autoclave. Isopropyl acetate was then added to the sample, and the synthesis of PPDA was continued with the reduction, step (b), with hydrazine. The remaining mixture in the autoclave was purged with nitrogen, then hydrogen and pressurized with hydrogen to 400 psig [28 atm or $2.8 \times 10^6$ Nm$^{-2}$]. The reaction was agitated at 15–25° C. for one hour. The reaction was vented, purged with nitrogen and isopropyl acetate added.

Following this, the organic layer separated. Analyses were by gas chromatography using a Varian 3400 G.C. equipped with a DB-I megabore column. Conversion to N-phenyl-p-phenylenediamine (PPDA) by hydrogenation was 6%. Conversion by hydrazine reduction was 66%.

As a result of this example, it was concluded that the hydrogenolysis does require a metal catalyst, whereas the oxidation can be done without one. However, it should be noted that it may be convenient to add the heterogeneous catalyst before the oxidation. The small amount of N-phenyl-p-phenylenediamine that was found may be due to electron transfer reactions during the oxidation.

Examples 8–10

The Performance of the Oxidation (step a) and Reduction (step b) Reactions to Yield PPDA Under a Range of Pressures The reactions of these Examples were run in a similar fashion to those previously described. In a 1 liter Magne-Drive autoclave using 76.0 g of three different batches of sodium pentacyanoammino ferrate (II), 37.2 g aniline, 4.0 g 5% Pd/C catalyst, 100 g ethylene glycol and 300 g distilled water were combined. The vessel was sealed, purged first with oxygen, then pressurized with oxygen to the desired pressure. The vessel was agitated at room temperature for 2.5 hours.

Following this oxidation, the vessel was purged first with nitrogen. Butyl acetate (200 ml) was pumped into the autoclave, which was then purged with hydrogen, and then pressurized with hydrogen to the desired pressure. The vessel was agitated at room temperature for 1.0 hr. After work up of the organic layer in the normal way, analyses by HPLC gave the conversions as presented in Table 2.

TABLE 2

| EXAMPLE | $O_2$ and $H_2$ PRESSURE, psig [atm] | CONVERSION % | YIELD (a) % |
|---|---|---|---|
| 8 | 400 [28] | 69 | 93 |
| 9 | 800 [56] | 63 | 88 |
| 10 | 100 [8] | 55 | 94 |

Notes for Table 2:
In column 2, the pressures shown are for both oxygen and hydrogen
(a) Yield based on aniline used.

Examples 11 and 12

Demonstration of the ability to recycle the sodium pentacyanoammino ferrate (II) complex In accordance with the previous examples, the reaction was run in a 1-liter Magne-Drive autoclave using 76.0 g sodium pentacyanoammino ferrate (II), 37.2 g aniline, 8.0 g. 5% Pd/C catalyst, 100 g ethylene glycol and 300 g distilled water. The vessel was sealed, purged first with oxygen and pressurized to 400 psig [28 atm or $2.8 \times 10^6$ Nm$^{-2}$] with oxygen. The vessel was then agitated at room temperature for 2.5 hours.

Following the oxidation, The vessel was purged first with nitrogen followed by the addition of 200 ml of butyl acetate pumped into the autoclave. Then the autoclave was pressurized with hydrogen to 400 psig [28 atm or $2.8 \times 10^6$ Nm$^{-2}$]. The autoclave was agitated at room temperature for 1.0 hour. The clave was opened, the solution filtered to remove the metal catalyst, and the layers were separated.

The ester layer was analyzed by gas chromatography, and the aqueous layer was returned to the autoclave. At this point, 37.2 g of aniline, and 8.0 g 5% Pd/C catalyst were added. The vessel was then sealed, purged first with oxygen and pressurized with oxygen to 400 psig [28 atm or $2.8 \times 10^6$ Nm$^{-2}$]. The mixture was agitated at room temperature for 2.5 hours, then purged with nitrogen. This was followed by the pumping of 200 ml butyl acetate into the autoclave. The vessel was then purged with hydrogen and pressurized with hydrogen to 400 psig [28 atm or $2.8 \times 10^6$ Nm$^{-2}$]. The mixture was agitated at room temperature for 1.0 hour.

The ester solution was analyzed by gas chromatography. The results of the analyses of both the fresh (example 11) and the recycled material (example 12) are shown in Table 3 in terms of both conversion and yield.

TABLE 3

| EXAMPLE | COMPLEX | CONVERSION % REL. AREA (a) | YIELD (b) % |
|---|---|---|---|
| 11 | FRESH | 69 | 95.6 |
| 12 | RECYCLE | 66 | 96.3 |

(a) GC analyses using a Perkin Elmer Model 8310 gas chromatograph with a one meter SP 2100 column.
(b) Based on aniline converted.

Examples 13–15

The Use of Ligands other than Ammonia for Pentacyano Ferrate (II) Complex and Recycle In accordance with the previous examples, the reaction was run in a 1-liter Magne-Drive autoclave using 42.8 g sodium pentacyanotrimethylamino ferrate (II), or the same amount of sodium pentacyanoisopropylamino ferrate (II), 18.6 g aniline, 4.0 g. 5% Pd/C catalyst, and 200.0 g distilled water. The vessel was sealed, purged first with oxygen and pressurized to 250 psig [18 atm or $1.8 \times 10^6$ Nm$^{-2}$] with oxygen. The vessel was then agitated at room temperature for 0.5 hours.

Following the oxidation, The vessel was purged first with nitrogen followed by the addition of 200 ml of butyl acetate pumped into the autoclave. Then the autoclave was pressurized with hydrogen to 400 psig [28 atm or $2.8 \times 10^6$ Nm$^{-2}$]. The autoclave was agitated at room temperature for 1.0 hour.

Following the agitation, the autoclave was opened and its contents removed. The mixture was then filtered and the aqueous and organic layers separated. The ester solution, contained in the organic layer, was analyzed by gas chromatography using a Perkin-Elmer Model 8310 Gas Chromatograph with a one meter SP2100 column, and the aqueous layer was returned to the autoclave.

At this point, 18.6 g of aniline, 4.0 g of 5% Pd/C catalyst was added. The vessel was then sealed, purged first with oxygen and pressurized with oxygen to 250 psig [18 atm or $1.8 \times 10^6$ Nm$^{-2}$]. The vessel was agitated at room temperature for 3.0 hours, followed by the pumping of 100 ml butyl acetate into the autoclave. The vessel was purged first with nitrogen and then with hydrogen and pressurized with hydrogen to 250 psig [18 atm or $1.8 \times 10^6$ Nm$^{-2}$]. The vessel was agitated at room temperature for 0.5 hour, after which time the autoclave was opened and the contents removed.

The ester solution was analyzed by gas chromatography, using the same equipment that has been specified in the earlier examples. The results of the analyses are presented in Table 4.

TABLE 4

| EXAMPLE | Ligand Used | CONVERSION % | YIELD (a) % |
|---------|-------------|--------------|-------------|
| 13 | trimethylamine | 89.5 | 96.9 |
| 14 | trimethylamine (1st recycle) | 63 | 95.9 |
| 15 | isopropylamine | 55 | 98.7 |

Notes for Table 4:
a) Yield based on aniline used

Examples 16–17
The Use of Non-Noble Metal Catalyst in Reduction (Step b) in Preparation of PPDA In accordance with the previous examples, the reaction was run in a 1-liter Magna-Drive autoclave using 57 grams of sodium pentacyanotrimethylamino ferrate (II), 27.9 g aniline, and 250 ml of distilled water. The vessel was sealed, purged first with oxygen and pressurized to 250 psig [18 atm or $1.8 \times 10^6$ Nm$^{-2}$] with oxygen. The vessel was then agitated at room temperature for three hours.

Following this oxidation, the vessel was purged first with nitrogen, then opened and the catalysts added. Then butyl acetate (200 ml) was added. The vessel was sealed, then with pressurized with hydrogen to the desired pressure of 400 psig [28 atm or $2.8 \times 10^6$ Nm$^{-2}$]. The catalysts used for the reduction, step b, were as shown in Table 5. The vessel was agitated at room temperature for 1.0 hr.

The ester solution was analyzed by gas chromatography, using the same equipment that has been specified in the earlier examples. The results of the analyses are presented in Table 5.

TABLE 5

| EXAMPLE | Catalyst Level | Catalyst; Time | CONVERSION % | YIELD (a) % |
|---------|----------------|----------------|--------------|-------------|
| 16 | 6.5 g (40% H$_2$O) | Raney Ni; 2.5 h | 48.1 | 92.0 |
| 17 | 6.1 g (50% H$_2$O) | 5% Pd/C; 0.5 h | 62.6 | 97.0 |

(a) Yield based on moles of aniline used

In view of the many changes and modifications that may be made without departing from principles underlying the invention, reference should be made to the appended claims for an understanding of the scope of the protection afforded the invention.

What is claimed is:

1. A method for preparation of substituted aromatic amines of formula (I) comprising the steps of:
   (a) oxidizing a solution of an aromatic amine of formula (II) in the presence of an oxidizing agent and a metal pentacyano ferrate (II) complex to form an arylenediaminopentacyanoferrate complex, said metal being selected from the group consisting of potassium and sodium wherein the pH of said solution is substantially equal to the pH of the metal pentacyanoferrate (II) complex in water; and
   (b) catalytically reducing said arylenediaminopentacyanoferrate complex with hydrogen using a heterogeneous metal catalyst, producing the corresponding substituted aromatic amine of formula (I)

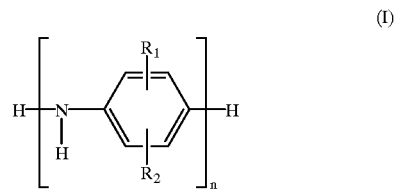

wherein n equals 2 to 5, and $R_1$ and $R_2$ are as set forth below;

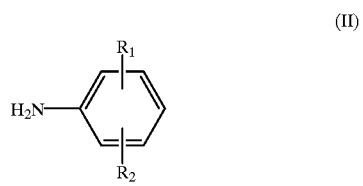

$R_1$ and $R_2$ may be the same or different, must be ortho or meta to the amino group, and may be hydrogen, $C_1$–$C_4$ alkyl, $C_1$–$C_4$ alkoxy, halogen, cyano, carboxylate salts and amides of carboxylic acids or mixtures thereof.

2. The method of claim 1 wherein the oxidizing agent is oxygen or hydrogen peroxide.

3. The method of claim 2 wherein the oxidizing agent is oxygen and a heterogeneous metal catalyst is present during said oxidizing step.

4. The method of claim 2 wherein the oxygen used is under pressure ranging from about 1 to 100 atmospheres.

5. The method of claim 2 wherein the oxygen in the oxidizing step and the hydrogen in the reducing step are used under pressures independently selected and ranging from about 2 to about 75 atmospheres.

6. The method of claim 1 wherein the metal pentacyano ferrate (II) complex is a trisodium pentacyano ferrate (II) complex containing water soluble ligands selected from the group consisting of ammonia, monoalkyl amines, dialkyl amines, trialkyl amines, N,N-dimethylaminoethanol, N,N,N',N'-tetramethylethylenediamine and pyridine.

7. The method of claim 6 wherein the trisodium pentacyano ferrate (II) complex has the structure Na$_3$[Fe(CN)$_5$NH$_3$.xH$_2$O], or its dimer.

8. The method of claim 1 wherein the heterogeneous metal catalyst is a supported or unsupported catalyst selected from the group consisting of palladium, platinum, ruthenium, rhodium, or nickel.

9. The method of claim 8 wherein the catalyst is platinum or palladium.

10. A method for producing N-phenyl-p-phenylenediamine comprising the steps of:
   a) oxidizing aniline in the presence of an oxidizing agent and a trisodium pentacyano ferrate (II) complex to form an N-phenyl-p-phenylenediaminopentacyano ferrate complex; and
   b) catalytically reducing the N-phenyl-p-phenylenediaminopentacyano ferrate complex with hydrogen using a heterogeneous metal catalyst to yield N-phenyl-p-phenylenediamine.

11. The method of claim 10 wherein a water-miscible organic solvent is added to solubilize the aniline and is selected from the group consisting of ethylene glycol, propylene glycol, diethylene glycol, triethylene glycol and mixtures thereof.

12. The method of claim 10 wherein the N-phenyl-p-phenylenediaminopentacyano ferrate complex is subjected to hydrogenation in the presence of a heterogeneous metal catalyst in the presence of a water immiscible solvent selected from the group consisting of butyl acetate, hexanol, 2-ethyl-1-butanol, hexyl acetate, ethyl butyl acetate, amyl acetate and substituted or unsubstituted aniline.

13. The method of claim 1 further comprising the steps of:
(c) recovering the metal pentacyanoferrate(II) complex which was reformed during the reducing step; and (c) recycling said complex by repeating said oxidizing step (a) using the recovered metal pentacyano ferrate(II) complex wherein the pH of said reformed metal pentacyanoferrate (II) complex is adjusted prior to recycle to a pH substantially equal to the pH of the metal pentacyanoferrate (II) complex in water.

14. The method of claim 1 wherein said oxidizing step is conducted in an aqueous medium.

15. The method of claim 1 wherein said oxidizing step (a) takes place at a temperature range from about 40° C. to about 60° C. and said reducing step (b) has a reaction temperature range from about 5° C. to about 60° C. for the reaction with hydrogen.

16. The method of claim 1 wherein pH of the reaction ranges from 10 to 12.

17. The method of claim 1 wherein pH of the reaction is maintained substantially at a pH equivalent to the solution of the dissolved metal pentacyano ferrate (II) complex in water.

* * * * *